United States Patent [19]
Viner

[11] Patent Number: 5,916,903
[45] Date of Patent: Jun. 29, 1999

[54] METHOD FOR REDUCING THE EFFECTS OF ANTINEOPLASTIC DISEASE TREATMENT

[75] Inventor: Norman Viner, Ottawa, Canada

[73] Assignee: Synapse Pahrmaceuticals International, Inc., Ottawa, Canada

[21] Appl. No.: 08/807,273

[22] Filed: Feb. 28, 1997

[51] Int. Cl.⁶ .................................................. A61K 31/44
[52] U.S. Cl. ........................................ 514/332; 514/640
[58] Field of Search ................................. 514/332, 640

[56] References Cited

U.S. PATENT DOCUMENTS

| | | |
|---|---|---|
| 2,816,113 | 12/1957 | Wilson et al. . |
| 2,947,782 | 8/1960 | Benneville et al. . |
| 2,996,510 | 8/1961 | Green . |
| 3,063,901 | 11/1962 | O'Leary et al. . |
| 3,077,476 | 2/1963 | Hackley, Jr. et al. . |
| 3,852,294 | 12/1974 | Hagedorn . |
| 3,928,594 | 12/1975 | Cook . |
| 4,002,760 | 1/1977 | Cook . |
| 4,352,810 | 10/1982 | Benschop et al. . |
| 4,581,224 | 4/1986 | Borch . |
| 4,594,238 | 6/1986 | Borch . |
| 4,620,973 | 11/1986 | Truog . |
| 4,675,326 | 6/1987 | Amitai et al. . |
| 4,865,837 | 9/1989 | Harris, III et al. . |
| 4,925,856 | 5/1990 | Harris, III et al. . |
| 4,938,949 | 7/1990 | Borch et al. . |
| 4,980,149 | 12/1990 | Antonetti et al. . |
| 4,988,710 | 1/1991 | Olney . |
| 5,002,755 | 3/1991 | Mitchell et al. . |
| 5,035,878 | 7/1991 | Borch et al. . |
| 5,206,371 | 4/1993 | Powers et al. . |
| 5,292,497 | 3/1994 | Schein et al. . |
| 5,294,430 | 3/1994 | Borch et al. . |
| 5,496,804 | 3/1996 | Reed et al. . |
| 5,661,142 | 8/1997 | Naeger ..................................... 514/178 |

FOREIGN PATENT DOCUMENTS 2016920  10/1979  United Kingdom .

OTHER PUBLICATIONS

Simon et al, "Administration of Obidoxime Tablets to Man", Arch. Toxicol, 36:83–88 (1976)

*Primary Examiner*—James H. Reamer

[57] ABSTRACT

A method is provided for alleviating the effects of antineoplastic disease treatment comprising administering to a mammal undergoing such treatment an acetylcholine esterase reactivator or prodrug derivative thereof optionally in association with an acetylcholine receptor antagonist.

23 Claims, No Drawings

METHOD FOR REDUCING THE EFFECTS OF ANTINEOPLASTIC DISEASE TREATMENT

BACKGROUND OF THE PRESENT INVENTION

The present invention is directed to a alleviating the effects of antineoplastic disease treatment.

The treatment of cancer by use of chemotherapy is presently commonplace. Such treatments may occur either alone or in conjunction with surgical removal of a tumor and/or radiation therapy. Such treatments are not without side effects to the patient. Chemotherapy agents which are toxic to cancer cells are also toxic to non-cancerous cells. The most susceptible cells of the patient are those having the highest rate of cell division; e.g., the bone marrow, hair and the gastrointestinal tract. A patient undergoing cancer treatment accordingly frequently suffers from nausea, vomiting, diarrhea, hair loss and lessened immune function (due to the lessened blood forming function of the bone marrow). It has also been found that administration of high levels of the therapeutic agent taxol may result in severe neurotoxicity in the form of peripheral neuropathy (see U.S. Pat. No. 5,496,804). Chemotherapeutic agents such as Adriamycin (doxorubicin hydrochloride) are also dose-limited due to the cardiotoxic effects of this agent.

Various methods have been proposed to lessen the toxic effects of antineoplastic disease treatment. See, for example, U.S. Pat. Nos. 4,581,224; 4,594,238; 4,620,973; 4,938,949; 4,980,149; 5,002,755; 5,035,878; 5,292,497; 5,294,430; and 5,496,804.

Unfortunately, none of the above methods of treatment have been very successful. The degree of success of such methods is generally not predictable due to the fact that the degree of success achieved is dependent upon the susceptibility of the patient to the particular treatment employed. In fact, it is now believed that some patients may be even more susceptible to the effects of treatment of antineoplastic disease by chemotherapy and/or radiation due to factors such as comorbid addictions and environmental factors. It is believed, for example, that xenobiotic toxic agents such as pesticides, insecticides, fungicides, heavy metals, oxidants, solvents and other environmental toxins encountered by the patient by various means (e.g., drinking water, food contamination, etc.) may enhance the susceptibilty of the patient to the toxic effects of such treatment. Such xenobiotic agents place stress on the nervous system (both central and peripheral) by inhibiting the ability of the nervous system to efficiently transmit nerve impulses along the synapse. The treatment of such a patient for antineoplastic disease may accordingly accentuate the degree of diminishment of function of the patient's nervous system, and hence the side effects suffered by the patient.

OBJECTS AND SUMMARY OF THE PRESENT INVENTION

It is accordingly an object of the present invention to provide a method for alleviating the side effects caused by antineoplastic disease treatment.

In accordance with the present invention, there is accordingly provided a method for alleviating the side effects caused by antineoplastic disease treatment of a mammal comprising administering to a mammal undergoing such treatment an effective amount of an acetylcholine esterase reactivator or prodrug derivative thereof optionally in association with an acetylcholine receptor antagonist.

DETAILED DESCRIPTION OF THE PRESENT INVENTION

The present invention involves the administration to a mammal of an effective amount of an acetylcholine esterase reactivator optionally in association with an acetylcholine receptor antagonist in order to reduce or alleviate the side effects of antineoplastic disease treatment.

Such antineoplastic disease treatment includes conventional therapies such as radiation and/or administration of a variety of chemotherapeutic agents. Such agents include but are not limited to cytotoxic antibiotics and associated derivatives (such as Adriamycin), antimetabolites (such as 5-fluorouracil), alkaloid-type compounds (such as alkaloids extracted from natural sources), DNA synthesis inhibitors and DNA crosslinkers (such as alkylating agents or heavy metal complexes), etc.

It is well known that acetylcholine esterase is essential to the transmission of nerve impulses across the synapse in the nervous system of the patient. In a patient whose nervous system function is diminished due to exposure to xenobiotic agents such as pesticides and/or fungicides (among others) which have the capability to diminish activity of the acetylcholine esterase at the synapse of the patient, treatment of antineoplastic disease in that patient with a therapeutic agent or by use of radiation which also has the affect of also diminishing function of the nervous system may place the patient at greater risk of side effects than might otherwise be the case. It has also been reported that a significant amount of acetylcholine esterase is synthesized in the bone marrow. Thus, to the extent that bone marrow function is diminished by such treatment, the availability of acetylcholine esterase for use in the nervous system may be reduced. It is accordingly desirable to counteract the effects of xenobiotic agents on the ability of acetylcholine esterase to function in the synapse either prior to or during treatment of antineoplastic disease to reduce the affect of such agents on the nervous system.

The acetylcholine esterase reactivators which may be employed in the present invention are well known to those skilled in the art and well-described in the literature. Such reactivators found early use as nerve gas and toxic pesticide poisoning antidotes. Exemplary acetylcholine esterase reactivators include but are not limited to those compounds disclosed in U.S. Pat. Nos. 2,816,113; 2,947,782; 2,996,510; 3,063,901; 3,077,476; 3,852,294; 3,928,594; 4,002,760; 4,352,810; 4,675,326; 4,865,837; 4,925,856; 4,988,710; 5,206,371 and U.K. application 2,016,920, each herein incorporated by reference in their entirety.

A preferred class of compounds which may be used as acetylcholine esterase reactivators are oximes. Oximes contain the moiety —CR=NOH and may generally be defined by the formula $(R^1-CR=NOH)^+ X^-$ where R is hydrogen, $C_{1-5}$ alkyl or $NH_2$ and $X^-$ is a pharmaceutically acceptable anion derived from a salt of an inorganic or organic acid. $R^1$ may take many forms. For example $R^1$ may be $C_{1-5}$ alkyl, aryl (e.g., phenyl), or a 5 or 6-membered heterocyclic moiety having from 1 to 3 nitrogen atoms in the heterocyclic ring.

The oxime may also be bicyclic in nature, as defined by the formula $(R^1CR=NOHX^-$ where R is hydrogen, $C_{1-5}$ alkyl or $NH_2$ and $R^1$ is

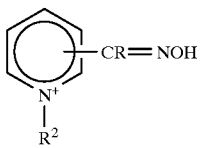

wherein R² is selected from the group consisting of:

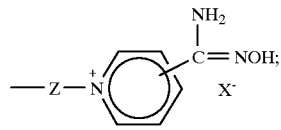

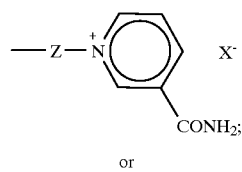

or

where Z is, for example, a polyalkylene group having from 1 to 6 carbon atoms, optionally including at least one ether linkage, such as —CH₂CH₂—, —CH₂OCH₂—, —CH₂CH₂OCH₂CH₂—, —CH₂OCH₂CH₂OCH₂—; or —(CH₂)n-phenyl-(CH₂)n— where n ranges from 1 to 6 and the phenyl moiety may be substituted by $C_{1-5}$ alkyl, and wherein X⁻ is a pharmaceutically acceptable anion derived from a salt of an inorganic or organic acid. The above formulae are intended to be merely illustrative and not limiting of the identity of the various types of oximes that may be employed in the present invention. Additional oximes not illustrated above exist which possess the ability to reactivate acetylcholine esterase and which may be employed with advantage in the present invention.

Exemplary acetylcholine esterase reactivators include the following oximes: 2-pyridine aldoxime methiodide, 4-pyridine aldoxime methiodide, methyl-2-pyridyl ketoxime methiodide, 1-methyl-pyridinium-2-aldoxime (2-PAM); 2,3-butanedione-2-oxime (DAM), pyruvaldehyde aldoxime (MINA), 2-pyridine aldoxime methochloride (2-PAM-Cl) (marketed as Protopam chloride), pralidoxime methylsulphate (marketed as Contrathion), obidoxime chloride (marketed as Toxogonin), 1,1'-polymethylene bis (4-formylpyridinium) halide oximes; 1,1'-(2,5-dimethyl-p-phenylenedimethylene) bis (4-formylpyridinium) halide dioximes; 1,1'-polymethylene bis (3-formylpyridinium) halide dioximes; 1,1'-(p-phenylenedimethylene) bis (3-formylpyridinium) halide dioximes; bis quaternary 4-formylpyriinium halide monooximes; 1,1'trimethylene bis (3-amidooximopyridinium) halides, quaternary pyridine aldoxime (TMB-4); HI-6; diacetyl monoxime; aldoxime-substituted triazolium compounds including 1,4-dimethyl-3-(hydroxyimino)methyl-1,2,4-triazolium chloride, 1-benzyl-3-(hydroxyimino)methyl-4-methyl-1,2,4-triazolium chloride, and 3-(hydroxyimino)methyl-1-methyl-4-(2'-methylsulfonyl-1'-ethyl)-1,2,4-triazolium chloride; and aldoxime-substituted imidazolium derivatives such as 1-([1'-(2'-butynyloxy)methyl]-2-(hydroxyimino)methyl-3-methylimidazolium chloride, 2-(hydroxyimino)methyl-3-methyl-1-[1'-2'-(methylsulfonyl)ethyloxy)methyl)-imidazolium chloride, 2-(hydroxyimino)methyl-3-methyl-1-[(2'-methyl-2'-nitropropyloxy)methyl]-imidazolium chloride, 1-[(2'-N,N-dimethylaminium)-1'-ethyl]2-(hydroxyimino)methyl-3-methylimidazolium chloride, 1-[2'-(hydroxyimino)methyl-3'-methyl-1'-imidazolo]-3-(4"-carbamoyl-1"-pyridino) propane dichloride, 1-(3'-bromopropyl-1'-oxy)methyl-2-(hydroxyimino)methyl-3-methylimidazolium chloride, 2-(hydroxyimino)methyl-3-methyl-1-(2'-pyrrdidinium-1'-)ethylimidazolium chloride hydrochloride, 1-(3'-butynyl-1'-thio)methyl-2-(hydroxyimino)methyl-3-methylimidazolium chloride, and 1-[(2'-N-ethyl-N-trifluoromethane sulfonyl)amino-1'-]ethyl-2-hydroxyimino)methyl-3-methylimidazolium chloride.

A preferred class of oximes suitable for use in the present invention may be depicted by the formula:

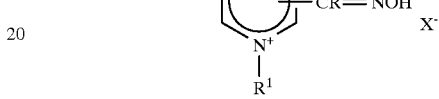

wherein R is hydrogen, $C_{1-5}$ alkyl, or NH₂; R¹ is $C_{1-5}$ alkyl (particularly methyl or ethyl), and X is an anion portion of the salt R¹X. Suitable acid addition salts include the chloride salt, the iodide salt and the methanesulfonate salt.

A specific oxime which is preferred for use in the present invention is 2-PAM chloride which is depicted by the following formula:

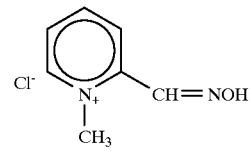

It is also advantageous to administer prodrug derivatives of oximes as disclosed in U.S. Pat. Nos. 3,929,813 and 3,962,447. Such prodrug derivatives exhibit an enhanced ability to pass the blood/brain barrier.

In addition to oximes, it has been found that hydrazone, semicarbazone and acyl hydrazone derivatives of 2-formyl-1-substituted pyridinium compounds may be usefully employed as acetylcholine esterase reactivators as described in U.S. Pat. No. 5,206,371, herein incorporated by reference.

The acetylcholine receptor antagonists which may optionally be employed in the present invention are well known to those skilled in the art and well-described in the literature. Exemplary antagonists include but are not limited to (singly or in combination) scopolamine, homatropine, atropine, methscopolamine, methylatropine, ipratropium, methyl-ecgonidine (MEG), mecamylamine, benactyzine, benztropine, trihexyphenidyl, biperiden, procyclidine, benzetimide, dexetimide, iaprophen and pharmaceutically acceptable derivatives thereof. See, for example, U.S. Pat. Nos. 5,011,853 and 5,552,407, herein incorporated by reference in their entirety, which disclose exemplary acetylcholine receptor antagonists. Preferred antagonists are scopolamine and ipratropium. Anticholinergic agents such as ipratropium bromide (Atrovent) are known for use in connection with the treatment of bronchoconstriction. See, Goodman & Gilman's *The Pharmacological Basis of Therapeutics,* 9th edition, 1996.

Acetylcholine esterase reactivators (such as 2-PAM and HI-6) have been used in conjunction with acetylcholine receptor antagonists (such as atropine) to provide in vivo protection against nerve gas agents and other organophosphate poisons. See, for example, U.S. Pat. Nos. 3,063,901; 4,713,391; 4,865,837; and 4,925,856. Atropine (an acetylcholine receptor antagonist) has also been used to treat bronchitis, nasal inflammation, hay fever, etc. as discussed in U.S. Pat. No. 1,794,292. However, an acetylcholine esterase reactivator such as oximes has not previously been employed to alleviate the side effects of antineoplastic disease treatment. The amounts of the respective components required to provide the benefits of the present invention are orders of magnitude less than the amounts normally administered to provide protection against nerve gas agents or toxic organophosphate poisoning.

In addition to the acetylcholine esterase reactivator and the acetylcholine receptor antagonist, it is within the scope of the present invention to co-administer additional compounds to assist in achieving the desired result or to provide additional cooperative treatment.

It may also be advantageous to administer a stimulant in association with the cholinesterase reactivator. A preferred stimulant is nicotine. Nicotine may be administered by any appropriate means, including nicotine gum, a nicotine patch, etc. Nicotine administration may occur prior to, during or subsequent to administration of the two compounds. It has been found that the amount of nicotine administered is less than the amount found in a patch or a stick of nicotine gum (e.g., one milligram or so, the amount not being particularly critical).

Other conventional stimulants (such as dopaminergic stimulants) may be administered in lieu of or in addition to nicotine. Such alternative stimulants include but are not limited to mineptine, Amphetamine, Amphetaminil, Bemegride, Benzphetamine, Brucine, Chorphentermine, Clofenciclan, Clortermine, Cocoa, Demanyl Phosphate, Dexoxadrol, Dextroamphetamine Sulfate (Dexedrine), Diethpropion, N-Ethylamphetamine, Ethamivan, Etifelmin, Etryptamine, Fencamfamine, Fenethylline, Fenosolone, Fenfluramine, Flurothyl, Hexacyclonate Sodium, Homocamfin, Mazindol, Megexamide, Methamphetamine, Methylphenidate, Nicotinic agonists, Nikethamide, Pemoline, Pentylenetetrazole, Phenidimetrazine, Phenmetrazine, Phentermine, Picrotoxin, Pipradrol, Prolintane, Pyrovalerone, and Tetrahydrobenzothienopyridines and mixtures thereof.

Xanthines are an additional class of compounds that may be administered in conjunction with the acetylcholine esterase reactivator and one or more of the other optional active ingredients to assist in signal modulation along the dendrite. U.S. Pat. Nos. 4,364,922; 4,980,379; 5,288,721; 5,340,813; 5,354,756; 5,440,041; 5,473,070; 5,567,704; 5,580,873; and 5,580,874 disclose exemplary xanthines which may be used in the present invention, each herein incorporated by reference. Exemplary xanthines include but are not limited to alkylxanthines such as propylxanthine and methylxanthine. Methylxanthines include 1,3,7-trimethylxanthine (caffeine), 3,7-dimethylxanthine (theobromine), 1,3-dimethylxanthine (theophylline), aminophylline, 1,8-dimethyl-3-(2-methyl-1-butyl)xanthine, 1,3-dimethyl-8-(n-propyl)xanthine, 1,4-(4-hydroxypentyl)-3,7-dimethylxanthine, and 7-(3-phenylpropenyl) theophylline. Exemplary propylxanthines include (E)-4-(1,2,3,6-tetrahydro-1,3-dimethyl-2,6-dioxo-9H-purin-8-yl) cinnamic acid and (E)-4-(1,2,3,6-tetrahydro-2,6-dioxo-1,3-dipropyl-9H-purin-8-yl)cinnamic acid. Prodrug forms of xanthines may also be employed as disclosed in U.S. Pat. No. 4,061,753, herein incorporated by reference. Such forms exhibit enhanced lipid solubility of the compound.

Adenosine antagonists may also be employed in conjunction with one or more of the above. Such compounds reduce the interstitial concentration of adenosine in myocardial tissue. The compounds may either be a competitive inhibitor or a substance that reduces the concentration of adenosine. A variety of compounds may be used as adenosine antagonists including xanthines (such as those discussed above), imidazopyrimidine, pyraxolopyridine, etazolate, pyrazoloquinoline and triazoloquinazoline. Exemplary adenosine antagonists are described in U.S. Pat. Nos. 4,364,922; 4,980,379; and 5,364,922, each herein incorporated by reference.

As still yet another compound which may be administered in conjunction with one or more of the above is the inhibiting neurotransmitter gamma-aminobutyric acid (GABA) or a precursor thereof such as L-glutamic acid. GABA receptor agonists and other antiepileptics may be employed such as Epival, Baclofen, Sabril, barbiturates, Gabapentin, Lamotrizine and Riluzolo.

It is also within the scope of the present invention to combine administration of the active ingredients with more conventional therapies such as antioxidant treatment, vitamin treatment, heavy metal antagonists such as chelating agents and bile-acid binding resins. The identity of such compounds is well known to those skilled in the art as described in Goodman & Gilman's *The Pharmacological Basis of Therapeutics,* 9th edition, 1996.

It is within the scope of the present invention to employ both pharmaceutically acceptable analogs as well as tautomers, isomers and salts of the above listed compounds. Analogs differ from the above compounds by means of added alkyl or aryl substituents, added or deleted halogen moieties, presence of differing linkages such as ether linkage, saturation or unsaturation. As to possible salts, the present invention includes within its scope pharmaceutically acceptable salts of alkali metals, alkaline earth metals, as well as acid addition salts of hydrochloric, hydrobromic, sulfuric, sulfamic, phosphoric, acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, etc.

The compounds of the present invention may be administered by any pharmaceutically acceptable means and in any pharmaceutically acceptable form. For instance, the compounds may be administered orally in the form of pills, tablets, solutions, syrups, lozenges, etc. in which the compound is the sole or co-ingredient as the active agent. The compounds may also be administered parenterally (e.g., intravenously, intramuscularly or subcutaneously) in association with a pharmaceutically acceptable carrier. Topical administration such as by transdermal patch is also acceptable. The active components may also be administered by inhalers or internasally.

Tablets or pills may contain the active ingredient(s) in admixture with conventional pharmaceutically acceptable excipients (i.e., inert diluents). Such tablets or pills may be uncoated or coated by conventional techniques to delay disintegration and absorption in the gastrointestinal tract. More specifically, such tablets or pills may include an enteric coating to ensure disintegration and absorption in the intestine. Such coatings are generally comprised of a cellulose lower fatty acid phthalate such as cellulose acetate phthalate.

It is preferred although not required that the acetylcholine receptor antagonist be administered prior to the administration of the acetylcholine esterase reactivator. Such sequential administration can be accomplished, for example, by administering the respective compounds by separate sequential oral or parenteral administration. Alternatively, the respective components can be sequentially administered in the form of a lozenge, tablet or pill which contains the two components in separate layers which will dissolve or disentegrate in sequence. Such sequential administration is not required, however.

The acetylcholine esterase reactivator and the acetylcholine receptor antagonist are employed or administered in an amount effective to reduce or prevent toxic symptoms of antineoplastic disease treatment. The phrase "reduce or prevent" is intended to refer to any degree of reduction of the symptoms suffered by the person.

With the above in mind, the various compounds of the present invention may be administered within a wide range of dosage levels while still enabling the benefits of the present invention to be achieved. For example, the acetylcholine receptor antagonist is administered at a dosage level of from 0.001 to 10 mg. The acetylcholine esterase reactivator is administered at a dosage level of from 1 mg to 10 mg. Such dosage levels are based on a standard adult body weight of 70 kg. Additional components such as stimulants are administered in amounts of from 0.1 to 10 mg. The xanthine component, if administered, will generally be administered in an amount of from 25 to 300 mg. Other components that may be co-administered such as anti-asthmatic drugs may be administered in conventional amounts. Such dosage administrations are repeated as required to provide the desired results, with administrations being repeated every 12 to 36 hours depending upon the extent of side effects observed.

From the above description, one of ordinary skill in the art can readily ascertain the essential characteristics of the present invention. Without departing from the scope of the present invention, various changes and/or modifications can be made which are still within the scope and range of equivalents of the attached claims.

What is claimed is:

1. A method for reducing or alleviating the effects of antineoplastic disease treatment in a mammal suffering from reduced activity of acetylcholine esterase at the synapse due to exposure to acetylcholine esterase-inhibiting xenobiotic agents, said method comprising administering to said mammal an acetylcholine esterase reactivator or pharmaceutically acceptable prodrug derivative thereof in an amount effective to increase activity of said acetylcholine esterase at the synapse in order to reduce or alleviate side effects of antineoplastic disease treatment to said mammal.

2. The method of claim 1 wherein an acetylcholine receptor antagonist is also administered to said mammal.

3. The method of claim 1 wherein said acetylcholine esterase reactivator is administered in a pharmaceutically acceptable carrier.

4. The method of claim 2 wherein said acetylcholine receptor antagonist is selected from the group consisting of scopolamine, homatropine, atropine, methscopolamine, methylatropine, ipatropium, mecamylamine and mixtures thereof.

5. The method of claim 1 wherein said acetylcholine esterase reactivator is an oxime or a pharmaceutically acceptable prodrug derivative thereof.

6. The method of claim 5 wherein said oxime is selected from the group consisting of monoquaternary oximes, bisquaternary oximes, and triquaternary oximes.

7. The method of claim 1 wherein said acetylcholine esterase reactivator is an oxime salt.

8. The method of claim 7 wherein said salt is an acid addition salt selected from the group consisting of a chloride, iodide and methanesulfonate salt.

9. The method of claim 8 wherein said acetylcholine esterase reactivator is a chloride salt of an oxime.

10. The method of claim 1 wherein said acetylcholine esterase reactivator is 2-pyridine aldoxime methochloride (2-PAM Cl).

11. The method of claim 1 wherein said acetylcholine esterase reactivator is selected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), pro-drug derivatives thereof and phamaceutically acceptable salts thereof.

12. The method of claim 1 wherein said mammal is a human.

13. The method of claim 1 wherein said antineoplastic disease treatment comprises chemotherapy.

14. The method of claim 2 wherein said acetylcholine receptor antagonist is selected from the group consisting of scopolamine and ipratropium, and said acetylcholine esterase reactivator is selected from the group consisting of an oxime, a pharmaceutically acceptable prodrug derivative thereof and a pharmaceutically acceptable salt thereof.

15. The method of claim 14 wherein said acetylcholine receptor antagonist is scopolamine and said acetylcholine esterase reactivator is 2-pyridine aldoxime methochloride (2-PAM Cl) or a pharmaceutically acceptable prodrug derivative thereof.

16. The method of claim 14 wherein said acetylcholine receptor antagonist is ipratropium and said acetylcholine esterase reactivator is 2-pyridine aldoxime methochloride (2-PAM Cl) or a pharmaceutically acceptable prodrug derivative thereof.

17. The method of claim 1 wherein said acetylcholine esterase reactivator is defined by the formula $(R^1-CR=NOH)^+ X^-$ where R is hydrogen, $C_{1-5}$ alkyl or $NH_2$, $R^1$ is $C_{1-5}$ alkyl and $X^-$ is a pharmaceutically acceptable anion derived from a salt of an inorganic acid or a salt of an organic acid.

18. The method of claim 1 wherein said acetylcholine esterase reactivator is defined by the formula $(R^1-CR=NOH)^+ X^{31}$ where R is hydrogen, $C_{1-5}$ alkyl or $NH_2$, $R^1$ is aryl and $X^-$ is a pharmaceutically acceptable anion derived from a salt of an inorganic acid or a salt of an organic acid.

19. The method of claim 1 wherein said acetylcholine esterase reactivator is defined by the formula $(R^1-CR=NOH)^+ X^-$ where R is hydrogen, $C_{1-5}$ alkyl or $NH_2$ and $R^1$ is a 5 or 6 membered heterocyclic moiety having from 1 to 3 nitrogen atoms in the heterocyclic ring and $X_-$ is a pharmaceutically acceptable anion derived from a salt of an inorganic acid or a salt of an organic acid.

20. The method of claim 1 wherein said acetylcholine esterase reactivator is defined by the formula $R^1CR=NOHX^-$ where R is hydrogen, $C_{1-5}$ alkyl or $NH_2$ and $R^1$ is

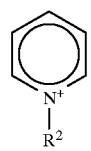

wherein R² is selected from the group consisting of:

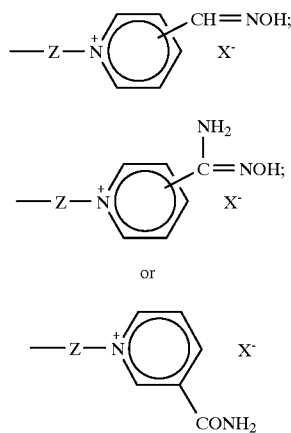

or where Z is a polyalkylene group having from 1 to 6 carbon atoms, optionally including at least one ether linkage, or —(CH₂)n-phenyl-(CH₂)n— where n ranges from 1 to 6 and the phenyl moiety may be optionally substituted by $C_{1-5}$ alkyl, and wherein $X^-$ is a pharmaceutically acceptable anion derived from a salt of an inorganic acid or a salt of an organic acid.

21. The method of claim 1 wherein said acetylcholine esterase reactivator is administered in an amount within the range of from about 1 to 9 mg per 70 kg body weight.

22. The method of claim 2 wherein said acetylcholine receptor antagonist is administered in an amount within the range of from about 0.001 to 9 mg per 70 kg body weight.

23. A method for reducing or alleviating the effects of antineoplastic disease treatment in a mammal whereby bone marrow function of said mammal is diminished as a result of such treatment, said method comprising administering to said mammal an acetylcholine esterase reactivator or pharmaceutically acceptable prodrug derivative thereof in an amount effective to enhance activity of acetylcholine esterase in the synapse to thereby reduce or alleviate side effects of such antineoplastic disease treatment.

* * * * *